US009473231B2

(12) United States Patent
Zahnd et al.

(10) Patent No.: US 9,473,231 B2
(45) Date of Patent: Oct. 18, 2016

(54) INSPECTION SYSTEM WITH WIRELESS DATA TRANSMISSION

(71) Applicant: iPEK International GmbH, Sulzberg (DE)

(72) Inventors: Fabian Zahnd, Kempten (DE); Peter Henn, Krugzell (DE); Gerhard Kennerknecht, Oberstdorf (DE)

(73) Assignee: iPEK International GmbH, Sulzberg (DE)

( * ) Notice: Subject to any disclaimer, the term of this patent is extended or adjusted under 35 U.S.C. 154(b) by 0 days.

(21) Appl. No.: 14/704,094

(22) Filed: May 5, 2015

(65) Prior Publication Data
US 2015/0318912 A1    Nov. 5, 2015

(30) Foreign Application Priority Data
May 5, 2014   (DE) .................. 20 2014 102 093

(51) Int. Cl.
| | |
|---|---|
| *G01N 21/00* | (2006.01) |
| *H04B 7/14* | (2006.01) |
| *B08B 9/032* | (2006.01) |
| *B08B 13/00* | (2006.01) |
| *G01N 21/954* | (2006.01) |
| *E03F 7/12* | (2006.01) |

(Continued)

(52) U.S. Cl.
CPC ............... *H04B 7/14* (2013.01); *B08B 9/032* (2013.01); *B08B 13/00* (2013.01); *E03F 7/12* (2013.01); *E03F 9/00* (2013.01); *G01N 21/954* (2013.01); *H04Q 9/00* (2013.01); *G01N 2021/9542* (2013.01); *G08C 17/02* (2013.01); *G08C 2201/40* (2013.01)

(58) Field of Classification Search
CPC ............ G01N 21/954; G02B 23/2407; G02B 23/2476; A61B 5/1076; G01M 3/38
USPC ........................................ 356/241.1
See application file for complete search history.

(56) References Cited

U.S. PATENT DOCUMENTS

| | | | |
|---|---|---|---|
| 5,383,605 A * | 1/1995 | Teague ................... | B05B 12/00 239/525 |
| 5,384,536 A * | 1/1995 | Murakami ............ | G01R 33/28 324/309 |

(Continued)

FOREIGN PATENT DOCUMENTS

| | | |
|---|---|---|
| DE | 102013101624 B3 | 10/2013 |
| DE | 102013100960 A1 | 4/2014 |
| JP | H09225060 A | 9/1997 |

OTHER PUBLICATIONS

German Search Report, dated Feb. 27, 2015, for German Application DE10 2014 106 251.5.

(Continued)

*Primary Examiner* — Tarifur Chowdhury
*Assistant Examiner* — MD M Rahman
(74) *Attorney, Agent, or Firm* — Myers Wolin, LLC

(57) ABSTRACT

Inspection system for inspection or cleaning of pipes (5), wherein the inspection system comprises an inspection or cleaning means (15) and a control means (10), and wherein the inspection system comprises a first transmission/receiver means (20; 40) assigned to the control means (10) and a second transmission/receiver means (30) assigned to the inspection or cleaning means (15) for wireless transmission of control or measurement data between the inspection or cleaning means (15) and the control means (10).

14 Claims, 3 Drawing Sheets

(51) Int. Cl.
*E03F 9/00* (2006.01)
*H04Q 9/00* (2006.01)
*G08C 17/02* (2006.01)

(56) References Cited

U.S. PATENT DOCUMENTS

| | | |
|---|---|---|
| 5,465,398 A | 11/1995 | Flammer |
| 7,050,535 B2* | 5/2006 | Georgeson ............ G01N 23/083 378/21 |
| 7,315,609 B2* | 1/2008 | Safai ...................... G01N 23/04 378/205 |
| 8,588,118 B2* | 11/2013 | Sakamoto ......... H04W 52/0229 370/311 |
| 2006/0055400 A1* | 3/2006 | Safai ...................... G01N 23/04 324/232 |
| 2007/0257197 A1* | 11/2007 | Gordon ................. G01T 1/2018 250/370.09 |
| 2009/0309967 A1* | 12/2009 | Kim ...................... G01N 21/94 348/143 |
| 2011/0054730 A1* | 3/2011 | Knight ................... G07C 5/008 701/29.5 |
| 2013/0072113 A1 | 3/2013 | Lee et al. |
| 2014/0073238 A1 | 3/2014 | Henn et al. |

OTHER PUBLICATIONS

European Search Report, dated Sep. 25, 2015, for European Application EP 15 16 6305.

* cited by examiner

INSPECTION SYSTEM WITH WIRELESS DATA TRANSMISSION

CROSS REFERENCE TO RELATED APPLICATIONS

This application claims priority under 35 U.S.C. §119 to German Application No. 20 2014 102 093.4, filed on May 5, 2014, the contents of which are incorporated by reference herein.

TECHNICAL FIELD

The invention relates to an inspection system for inspection and/or cleaning of pipes, which is adapted to transmit control and/or measurement data wirelessly, as well as to a repeater for the inspection system according to the invention for increasing the operation range of a wireless communication connection.

BACKGROUND

In the field of sewer inspection and/or sewer cleaning it is known to use sewer inspection systems or sewer cleaning systems, which may be inserted into the pipe or sewer pipe to be inspected, and which may be moved within the sewer pipe. For cleaning of sewer pipes, it is known to use cleaning devices, as high pressure rinsing devices. The sewer inspection systems as well as the cleaning devices may comprise sensors by means of which different measurement data can be acquired during the inspection or during the cleaning The sewer inspection systems or cleaning devices may also comprise cameras, by means of which the sewer pipe's interior may be inspected optically.

The acquired measurement data or image data have to be transmitted to a control means arranged exterior of the pipe system, where it is possible to analyze and, if needed, further process it. For this, it is known to connect the sewer inspection systems or cleaning devices via a cable connection to the control means. With respect to data transmission via cable connections, however, the limited transmission length due to the limited length of the cable connection is disadvantageous.

FIG. 1 shows a first solution known from prior art, according to which the cleaning device or cleaning means 15 is coupled to a control means 10 via a rinsing hose 17. In addition to the rinsing hose 17, data and/or power cables are provided, in order to transmit data from the cleaning device or cleaning means 15 to the control means 10.

In order to nevertheless be able to inspect or clean longer passages, the entire inspection or cleaning system has to be displaced, as shown in FIG. 2. As can be seen from FIG. 2, the control means 10 has to be displaced or passed over to the next drain 6 to be able to inspect or clean the next or a further pipe or sewer section.

Therefore, it is an object of the present invention to at least partially avoid the disadvantages known from prior art, and to provide solutions, according to which the operation range of a wireless communication connection between a transmission means and a receiver means arranged outside of the sewer can be increased, and to be able to inspect or clean substantially longer pipe or sewer sections in a single working step without the control means or various reflectors having to be displaced.

SUMMARY

According to the invention, this object is solved according to the independent claims by an inspection system for inspection and/or cleaning of pipes as well as a repeater for the inspection system according to the invention. Preferred embodiments or further developments of the invention are specified in the respective dependent claims.

Accordingly, an inspection system for inspection and/or cleaning of pipes is provided, wherein the inspection system comprises an inspection and/or cleaning means and a control means, and wherein the inspection system comprises a first transmission/receiver means assigned to the control means and a second transmission/receiver means assigned to the inspection and/or cleaning means for wireless transmission of control and/or measurement data between the inspection and/or cleaning means and the control means.

The inspection system may comprise at least one repeater having an antenna system or having at least one antenna, which is operatively arranged between the first transmission/receiver means and the second transmission/receiver means and which is adapted to increase the operation range of a wireless communication connection established between the first transmission/receiver means and the second transmission/receiver means.

The wireless communication connection may comprise a WLAN communication connection.

The at least one repeater may be arranged in the pipe to be inspected and/or to be cleaned.

The inspection and/or cleaning means may be coupled and/or connected to the control means by means of a hose, a rope, or a cable.

The at least one repeater may be connected to the hose, to the rope, or to the cable. Thereby, it is guaranteed that the repeaters move in a certain distance with respect to the transmission means, in order to maintain an interruption-free wireless communication connection to the receiver means.

According to an embodiment of the invention, in addition to the hose, rope, or cable, which couples or connects the inspection and/or cleaning means to the control means, an additional hose, an additional rope, or an additional cable may be provided, which is insertable into the pipes, wherein the at least one repeater may be fixed to the additional hose, additional rope, or additional cable.

The at least one repeater may be fixed releasably.

According to an embodiment of the invention, the at least one repeater may be fixed to a hose, wherein the hose connects the inspection and/or cleaning means to the control means. Hereby, that hose may comprise a rinsing hose, via which rinsing water is supplied to the cleaning means.

The inspection and/or cleaning means may comprise a rinsing means, in particular, a rinsing nozzle.

According to an embodiment of the invention, the rinsing nozzle may comprise a camera, wherein images taken by the camera may be transmitted to the first transmission/receiver means via the second transmission/receiver means, and/or wherein control commands intended for the camera and/or rinsing nozzle may be transmitted to the second transmission/receiver means via the first transmission/receiver means wirelessly.

It is advantageous, if the at least one repeater is fixed to the hose releasably by means of fixing means, in particular, clamps or clips. Thereby, the at least one repeater may be fixed to the hose at different locations.

According to an embodiment of the invention, the hose may comprise at least two hose sections separated from each other, wherein the at least one repeater may be arranged between the two hose sections, and connects the two hose sections to each other.

The two hose sections may respectively comprise a hose coupling, by means of which the hose sections may be connected to the repeater.

Hereby, it is advantageous, if the repeater has an axial duct, which connects the first hose section to the second hose section.

Advantageously, the diameter of the axial duct may be substantially equal to the diameter of the first and the second hose sections.

In a specifically preferred embodiment of the invention, the repeater may comprise a device for converting kinetic energy of the rinsing water into electrical energy, wherein the device has at least one hydraulic turbine and at least one generator, wherein at least the hydraulic turbine is at least partially arranged within the axial duct of the repeater.

Further, the repeater may comprise an accumulator, which is coupled to the generator, wherein the accumulator and/or the generator supplies the repeater with electrical energy.

According to an embodiment of the invention, the at least one repeater is integrated into the liner of the hose.

According to a further embodiment of the invention, the at least one repeater may be arranged at an inner wall of the hose and may be surrounded by a substantially watertight liner.

With respect to an arrangement of the repeater within the liner or at the inner wall of the hose, it is preferable, if the antenna of the repeater is led at least partially through the liner of the hose to the outside.

The antenna of the repeater may be formed by a material suitable for an antenna being arranged at the outer wall of the hose.

According to an embodiment of the invention, the material suitable for an antenna may surround the liner of the hose in a radial direction at least partially. Thereby, the uniform dispersion of the radio signal may be guaranteed substantially independent of a radial rotation of the hose.

According to a preferred embodiment of the invention, a number of repeaters may be provided, wherein the repeaters preferably are arranged in equal distances with respect to each other or in equal distances with respect to each other at the hose.

According to an embodiment of the invention, the inspection system may comprise a stationary repeater, by means of which a wireless communication connection between the first transmission/receiver means and the first repeater may be arranged in a moving direction, i.e., the repeater, which has the least distance to the stationary repeater may be established.

Moreover, a repeater for an inspection system for inspection and/or cleaning of pipes is provided by the invention, wherein the repeater comprises at least one antenna or an antenna system, and is adapted to increase the operation range of a wireless communication connection between a first transmission/receiver means and a second transmission/receiver means arranged in the pipe.

The repeater may comprise fixing means, by means of which it may be connected to a hose, in particular, a rinsing hose, at a cable, or at a rope, preferably releasably.

The repeater may comprise an axial duct, by means of which a first rinsing hose may be connected to a second rinsing hose, wherein for connecting the two rinsing hoses to the repeater, hose couplings are provided.

It is preferable, that the diameter of the axial duct of the repeater may be substantially as large as the inner diameter of the first and second rinsing hoses.

The repeater may comprise a device for conversion of kinetic energy of the rinsing water into electrical energy, wherein the device comprises at least one hydraulic turbine and at least one generator, wherein at least the hydraulic turbine is arranged within the axial duct of the repeater at least partially.

The repeater may preferably be adapted to automatically increase and/or automatically decrease its transmission power.

It is preferable, that the repeater is accommodated within a substantially watertight and/or pressure tight housing, whereby only the antenna is led from the housing to the outside, and whereby a part of the housing forms the antenna of the repeater.

Moreover, a transmission/receiver means for wireless transmission of control and/or measurement data between an inspection and/or cleaning means assigned to the transmission/receiver means and a controller means of an inspection system for inspection and/or cleaning of pipes is provided, wherein the transmission/receiver means is adapted for establishing a wireless communication connection to a further transmission/receiver means assigned to the control means.

The transmission/receiver means may be adapted to establish a wireless communication connection to a repeater according to the invention arranged between the transmission/receiver means and the further transmission/receiver means.

The transmission/receiver means may be arranged at the inspection and/or cleaning means, wherein the inspection and/or cleaning means comprises at least one selected from the group comprising a cleaning nozzle, an inspection camera, an inspection and/or cleaning vehicle, and combinations thereof.

It is preferred, that the transmission/receiver means may be coupled to the inspection and/or cleaning means releasably, wherein the transmission/receiver means comprises electrical contact members, which correspond to electrical contact members of the inspection and/or cleaning means.

The transmission/receiver means may be arranged in a substantially watertight and preferably explosion-proof housing.

Further, an inspection and/or cleaning device is provided comprising a transmission/receiver means according to the invention and an inspection and/or cleaning means which may be coupled to the transmission/receiver means.

The inspection and/or cleaning means may comprise at least one selected from the group consisting of a cleaning nozzle, an inspection camera, an inspection vehicle and/or cart, and combinations thereof The inspection and/or cleaning means may comprise a cleaning nozzle with an inspection camera integrated in the cleaning nozzle, wherein the inspection camera preferably may be arranged within the cleaning nozzle releasably, and wherein the inspection camera is coupled operatively to the transmission/receiver means.

A power supply, in particular, an accumulator, may be provided at the vehicle, which is coupled to the transmission/receiver means.

BRIEF DESCRIPTION OF THE DRAWINGS

Further details and features of the invention as well as concrete, in particular, preferred embodiments of the invention can be derived from the following description in connection with the drawing, in which.

DETAILED DESCRIPTION

Figure 1:
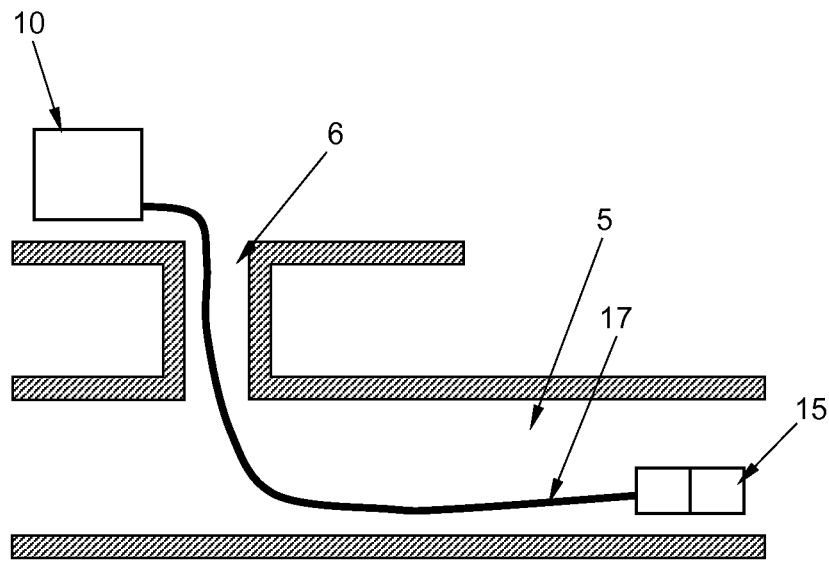
FIG. 1 shows an inspection system known from prior art.
Figure 2:
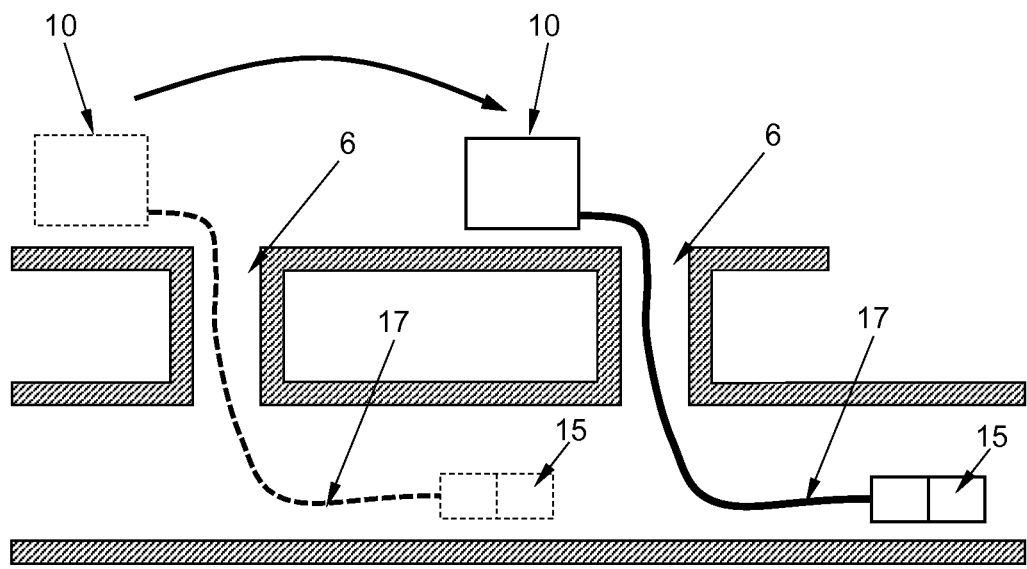
FIG. 2 shows a further inspection system known from prior art.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise.

Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

This disclosure describes the best mode or modes of practicing the invention as presently contemplated. This description is not intended to be understood in a limiting sense, but provides an example of the invention presented solely for illustrative purposes by reference to the accompanying drawings to advise one of ordinary skill in the art of the advantages and construction of the invention. In the various views of the drawings, like reference characters designate like or similar parts.

Figure 3:
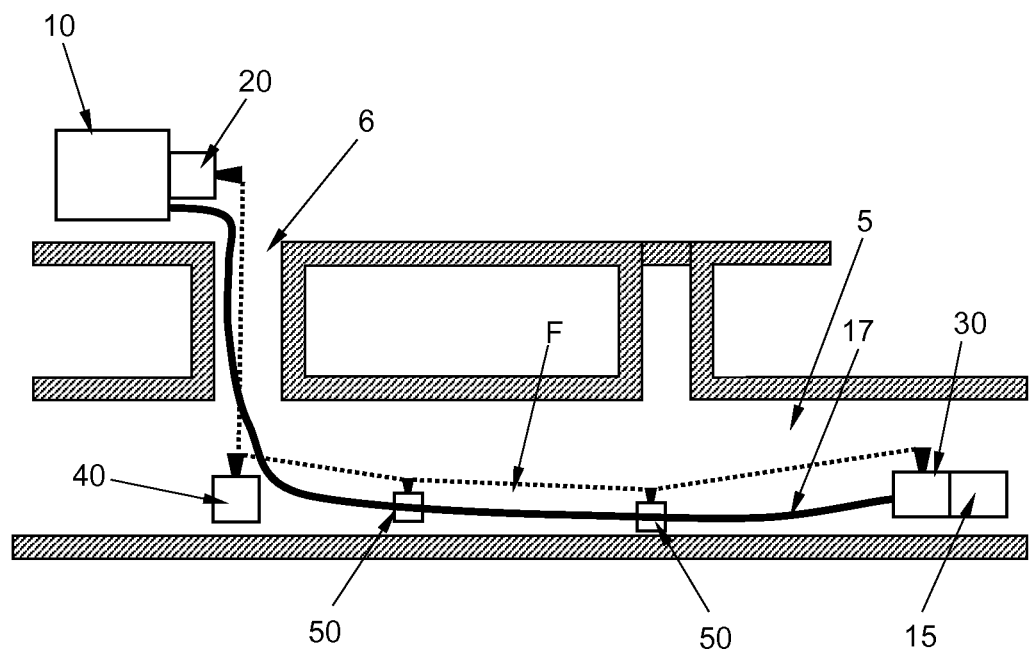
FIG. 3 shows an example of the inspection system according to the invention.

FIG. 3 shows an inspection system according to the invention, which comprises an inspection vehicle or a control means 10 and an inspection and/or cleaning means 15. The inspection and/or cleaning means 15 may comprise a camera and/or rinsing nozzle. According to an embodiment of the invention, the inspection and/or cleaning means 15 is embodied as a rinsing nozzle, at the front end of which a camera is arranged such that during the cleaning procedure, at the same time, the success of the cleaning procedure may be monitored. According to an alternative embodiment, the inspection and/or cleaning means may comprise a cart, at which various sensor means and/or camera means may be arranged.

With respect to the example of an inspection system according to the invention shown in FIG. 3, the inspection and/or cleaning means 15 embodied as cleaning nozzle is connected to the inspection vehicle or to the control means 10 via a rinsing hose 17. Via the rinsing hose 17, rinsing water is supplied to the rinsing nozzle, which exits from the rinsing nozzle with high pressure in order to clean the inner walls of the pipe 5. The rinsing hose 17 may also be arranged on a reel, and may be wound around or unwound from the reel.

A first transmission/receiver means 20 is assigned to the inspection vehicle or the control means 10, which comprises a transmission/receiver module with a corresponding transmission/receiver antenna. A second transmission/receiver means 30 is assigned to the inspection and/or cleaning means 15, which also comprises a transmission/receiver module with a transmission or receiver antenna.

According to the invention, now, a wireless communication connection F is established between the first transmission/receiver means 20 assigned to the inspection vehicle or the control means 10 and the second transmission/receiver means 30 assigned to the inspection and/or cleaning means 15, via which a data exchange between the control means 10 and the inspection and/or cleaning means 15 is executed. For example, via the wireless communication connection F, the video or image data taken by an inspection camera may be transmitted to the control means 10. Alternatively or additionally, control commands, for example, control commands by means of which the rinsing nozzle and/or the camera may be controlled, may be transmitted from the control means 10 via the wireless communication connection F to the inspection and/or cleaning means 15.

The communication connection F, for example, may be embodied as WLAN connection. The provision of a WLAN communication connection has the advantage that no special official permit is necessary for pipe inspection systems or pipe cleaning systems.

In order to avoid that with increasing advance or increasing feed of the inspection and/or cleaning means 15 into the pipe 5, the control means 10 has to be displaced, as it is necessary with respect to systems known from prior art, according to the invention it is provided that one or more repeaters 50 are arranged between the first transmission/receiver means 20 and the second transmission/receiver means 30. By utilizing the repeaters, the operation range of a signal, for example, a signal radiated from the second transmission/receiver means 30, may be substantially increased.

Hereby, the repeater is adapted to receive the signals of a transmitter, for example, the second transmission/receiver means, and to further transmit them in a newly processed form, wherein a larger distance between transmitter and receiver can be bridged. Optionally, the repeaters 50 may be adapted to remove noise as well as distortions of the runtime and the pulses shape from the received signal such that a newly processed signal may be transmitted further. According to an embodiment of the invention, so called WLAN repeaters for increasing the operation range of the wireless communication connection F may be provided.

According to the embodiment of the system according to the invention shown in FIG. 3, also a stationary repeater 40 may be provided, which is arranged at the bottom of the pipe drain 6, and which further transmits the signal received from the next repeater 50 through the pipe drain to the outside to the first transmission/receiver means, or sends the signal received from the first transmission/receiver means further to the next repeater 50. The connection between the control means 10 and the stationary repeater 40 may be effected by wires or wireless. The wireless connection between the control means 10 and the stationary repeater 40 may be embodied as WLAN connection.

The repeaters 50 are arranged at the rinsing hose 17 in more or less equal distances. Preferably, the repeaters 50 are connected to the rinsing hose releasably such that the distance between the repeaters 50 may be adapted to the conditions prevailing in the pipe 5 in order to establish or to maintain a preferably optimal wireless communication connection between the first transmission/receiver means 20 and the second transmission/receiver means 30, and at the same time, to use as few repeaters as possible.

In a variant of the invention, the repeaters 50 can be fixed during the insertion of the rinsing hose 17 into the pipe 5 at it. The connection of the repeaters to the hose 17, hereby, may be carried out automatically or manually. For connecting the repeaters 50 to the hose 17, a connection unit may be provided at the inspection vehicle, which connects the repeaters to the hose 17. The distance provided between the two repeaters 50 may depend on the signal strength or on the operation range.

In an alternative embodiment of the system according to the invention, the repeaters 50 may be connected to the hose 17 fixedly, i.e., the repeaters remain on or at the hose and are wound or wound up with it. In yet a further embodiment of the system according to the invention, the repeaters may also be arranged within the hose, for example, in the hose liner or in the hose interior, or the repeaters may be arranged between two hose sections.

According to an alternative embodiment, it is moreover possible to bring the repeaters into the pipe 5 independently of the hose 17 by providing, for example, a cable or a rope, which is brought into the pipe 5 together with the hose 17, and which can be fixed or is fixed to the repeaters 50.

The fixing of the repeaters to the rinsing hose 17 or to the cable or to the rope has the advantage that during the advancing of the inspection and/or cleaning means 15 in the pipe 5, the distance of the repeaters 50 with respect to each other or the distance of the first repeater to the second transmission/receiver means 30 basically always remains the same, leading to qualitatively uniform communication connections over the time, when optimal conditions of the surroundings are prevailing within the pipe 5.

However, usually no such optimal surrounding conditions are prevailing within a pipe such that the operation range of a signal radiated from a repeater may fluctuate, leading in the most unfavorable case to an interruption of the connection of the wireless communication connection F. In order to substantially avoid such interruptions of the communication connection F, it may be provided for the repeaters 50 being adapted to automatically increase and/or automatically decrease their transmission power. In case a repeater 50 determines that a signal received from an adjacent repeater is too low or falls below a predetermined threshold value, the repeater 50 may instruct the adjacent repeater to increase its transmission power. On the other hand, if a repeater determines that the signal received from its adjacent repeater is too strong or exceeds a predetermined threshold value, the repeater 50 may instruct the adjacent repeater to reduce the transmission power, whereby the energy consumption of the repeaters is reduced, and at the same time, a sufficient signal strength is guaranteed for an optimal data transmission via the communication connection F.

Instead of the stationary repeater 40 shown in FIG. 3, one or more additional repeaters 50 may be provided in the area, in which the hose is redirected by the drain 6 into the pipe 5. However, the provision of a stationary repeater 40 at the bottom of the drain 6 is not problematic, because the correct orientation of the stationary repeater may substantially be omitted without substantially affecting the wireless communication connection F.

The system according to the invention having a number of repeaters between the first transmission/receiver means 20 and the second transmission/receiver means 30 has the advantage that the inspection and/or cleaning means 15 may advance within the pipe 5 arbitrarily far without having to displace the inspection vehicle or the control means or the first transmission/receiver means 20, whereby it nevertheless is guaranteed that a wireless communication connection F between transmitter and receiver can be established and maintained. Thereby, cleaning and/or inspection procedures may be shortened substantially.

Figure 4:
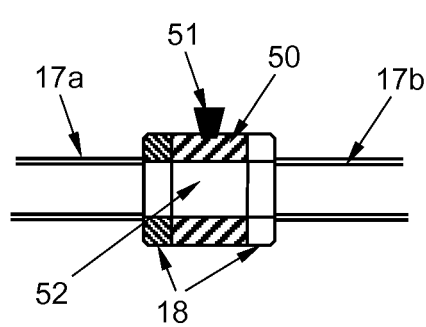
FIG. 4 shows an example of a repeater according to the invention for an inspection system according to the invention.

FIG. 4 shows an example of a repeater according to the invention for an inspection system according to the invention.

The repeater 50, here, is arranged between a first rinsing hose 17a and a second rinsing hose 17b, wherein for connecting the two hose end pieces to the repeater 50, hose couplings 18 are provided at the respective hose end pieces. The repeater 50 has an axial duct 52, the inner diameter of which may be as large as the inner diameter of the two rinsing hoses 17a, 17b.

In FIG. 4, an antenna system 51 of the repeater 50 is shown schematically. According to a concrete embodiment of the repeater 50, the antenna system 51 is configured such that it is substantially protected from external influences.

For the operation of the repeater 50, a power supply is necessary, for which, for example, an accumulator not shown in FIG. 4 may be provided. In a further embodiment of the inventive repeater according to FIG. 4, for the supply of the repeater 50 with electrical energy, a device for converting kinetic energy of the rinsing water into electrical energy may be provided, whereby the device may comprise a hydraulic turbine or a generator assigned to the hydraulic turbine. The hydraulic turbine may be arranged in the repeater 50 such that it protrudes at least partially into the axial duct 52 such that the rinsing water flowing through the axial duct 52 is able to actuate the hydraulic turbine. In an embodiment of the repeater 50, the generator may supply the repeater 50 directly with electrical energy. Alternatively, the generator may also be coupled to the accumulator in order to charge the accumulator.

Figure 5:
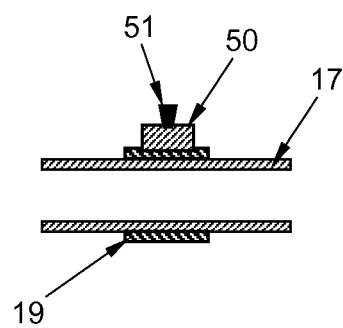
FIG. 5 shows an alternative example of a repeater according to the invention for an inspection system according to the invention.

FIG. 5 shows an alternative embodiment of the inventive repeater 50. The repeater 50 comprises fixing means 19, by means of which the repeater 50 may be connected to the hose 17, preferably releasably. As fixing means 19, for example, clips or clamps may be provided. This embodiment has the advantage that the repeater 50 may be fixed to the rinsing hose 17 at any arbitrary location. Preferably, in this embodiment of the repeater, the repeater comprises an accumulator in order to supply the repeater with electrical energy. According to this embodiment it has to be guaranteed in any case that the repeater 50 is accommodated within a substantially watertight and/or pressure tight housing, wherein the antenna system 51 may be led out of the housing.

Figure 6:
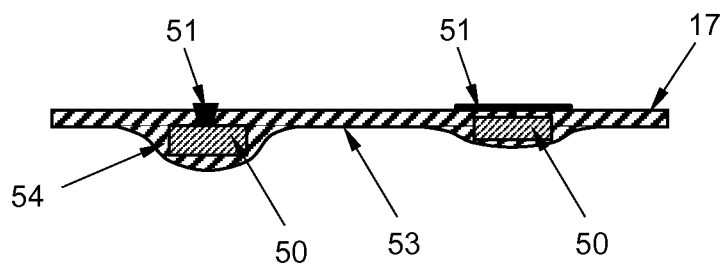
FIG. 6 shows variants of a repeater according to the invention, which are integrated in a hose liner.

FIG. 6 shows a further alternative embodiment of a repeater 50 and its arrangement at the rinsing hose 17.

The repeater 50 on the left-hand side shown in FIG. 6 is arranged at an inner wall 53 of the rinsing hose 17, and is surrounded by a liner, which closes the repeater 50 in a substantially watertight and/or pressure tight manner. The liner 54 may be made from the same material as the liner of the rinsing hose 17. The antenna system 51 of the repeater 50 is led through the pipe liner of the pipe to the outside such that a radiation of the signals may result substantially without interference by the pipe liner. Because the repeater 50 is only arranged at a location in the interior of the rinsing hose 17 at the hose inner wall, the cross section of the rinsing hose is only reduced slightly.

The repeater 50 on the right-hand side shown in FIG. 6 is at least partially embedded in the liner of the rinsing hose 17 such that only a part of the repeater projects into the hose interior. Also here, the part of the repeater 50 protruding into the hose interior is surrounded by a liner, which surrounds the repeater 50 in a substantially watertight and/or pressure tight manner. Contrary to the left repeater 50, with respect to the right repeater 50, the cross section of the rinsing hose is even less reduced such that the flow of the rinsing water is even less affected.

With a sufficiently large liner thickness of the rinsing hose 17, the repeater 50 may also be integrated in the liner completely such that the repeater 50 does not project into the interior of the hose 17.

At the outer wall of the hose 17, a planar material suitable as antenna is applied. This planar material may be connected to the repeater 50 through the pipe liner. According to a preferred embodiment, this antenna suitable material may surround the liner of the hose in the radial direction such that the antenna suitable material substantially forms an annular antenna 51 surrounding the hose. Advantageously, the operation range of the signals radiated from the antenna is substantially independent of a radial rotation of the hose.

The repeaters integrated in the rinse liner may comprise an accumulator for power supply of the repeater.

Figure 7:
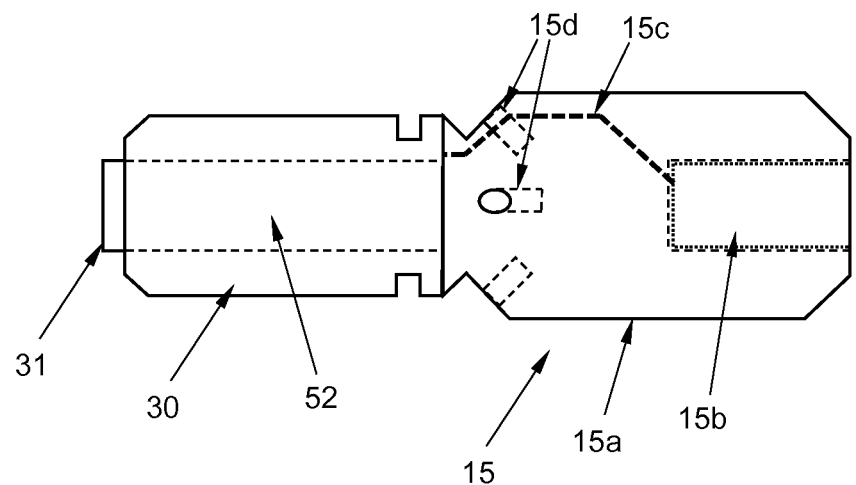
FIG. 7 shows an inspection and/or cleaning device according to the invention with a cleaning nozzle.

FIG. 7 shows an inspection and/or cleaning device according to the invention having a cleaning means embodied as cleaning nozzle or rinsing head or rinsing nozzle 15*a*, and the transmission/receiver means 30 according to the invention. The transmission/receiver means 30 preferably is arranged at the rear end of the rinsing nozzle 15*a* releasably. Contact pins corresponding to each other are provided at the transmission/receiver means 30 and at the rinsing nozzle 15*a*, via which an electrical connection between the transmission/receiver means 30 and the rinsing nozzle 15*a* can be established.

At the rear end of the transmission/receiver means 30, a hose port 31 is provided, to which a rinsing hose may be connected. The hose port 31 connects the rinsing hose to an axial duct 52, the diameter of which may correspond to the diameter of the rinsing hose. The rinsing water is supplied to the rinsing nozzle 15*a* through the duct 52, where it may exit through a number of nozzles 15*d* to the exterior with high pressure.

The rinsing nozzle 15*a* has at the front end an axial recess, into which a camera or camera system 15*b* can be inserted. The camera 15*b* preferably may be arranged within the axial recess releasably such that the camera may be exchanged in a simple manner. Via a power or data cable 15*c*, the camera 15*b* is coupled to the transmission/receiver means 30, wherein the power or data cable 15*c* may be arranged within a cable channel provided in the rinsing head 15*a*. Preferably, the power or data cable 15*c* is connected to a number of contact pins.

The transmission/receiver means 30 is accommodated in a substantially watertight and preferably explosion-proof housing. The shape of the housing or the outer contours of the transmission/receiver means 30 are preferably selected such that they do not interfere with the rinsing water exiting from the nozzles 15*d*.

The images taken by the camera 15*b* are transmitted to the transmission/receiver means 30 via the data cable 15*c*, from where they can be transmitted to a further transmission/receiver means 20 or a repeater 50 according to the invention wirelessly.

The coupling of the transmission/receiver means 30 to the rinsing nozzle 15*a* may, for example, be affected by means of a screw connection or by a plug connection, whereby a sealing ring preferably may be arranged between the transmission/receiver means 30 and the rinsing head 15*a*.

According to an embodiment of the invention, the rinsing head 15*a* may be configured in one piece. It may, however, also be made from two or more pieces. The transmission/receiver means 30 may also be configured in one piece or in several pieces. According to an embodiment of the invention it may be provided for the rinsing nozzle 15*a* and the transmission/receiver means 30 being configured in one piece.

Figure 8:
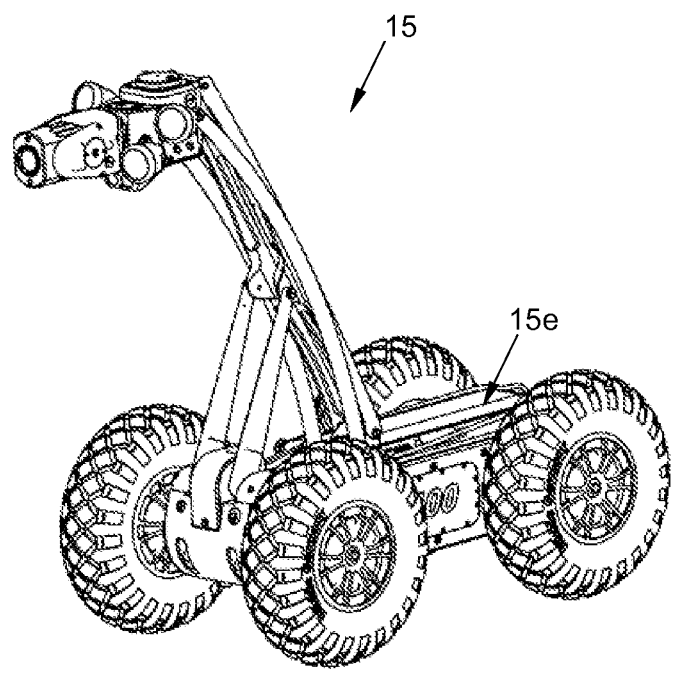
FIG. 8 shows an inspection and/or cleaning device according to the invention with a cart.

FIG. 8 shows an inspection and/or cleaning device according to the invention with a cleaning means configured as a cart or inspection vehicle at which a transmission/receiver means 30 is arranged according to the invention. The transmission/receiver means 30, here, is arranged or accommodated in the cart body or in the cart housing 15*e*. Alternatively, the transmission/receiver means 30 may also be arranged as a superstructure at the cart. The cart, here, further has a power supply, preferably an accumulator, such that the cart may be advanced into the pipe, for example, for inspection of a pipe without any attachments, as cables or the like. The data transmission from or to the cart is carried out wirelessly via the transmission/receiver means 30 arranged at or in the cart.

Thereby, it is avoided that the cart has to drag cables or the like, which, in particular, during inspection trips in long pipes is an advantage.

Camera systems or other sensors, actuators, etc. may be, for example, arranged at the cart, which are coupled to the transmission/receiver means 30 operatively.

Accordingly, by means of the present invention, it is possible to introduce any appliance provided with a second transmission/receiver means into a pipe and to advance it in the latter, wherein a wireless communication between the second transmission/receiver means and the first transmission/receiver means arranged outside of the pipe is possible independent of the position of the second transmission/receiver means in the pipe, in that a number of repeaters are provided between the two transmission/receiver means by means of which the operation range of the wireless communication connection is increased.

REFERENCE NUMERALS

5 pipe (e.g., sewer pipe)
6 drain (e.g., sewer drain)
10 inspection vehicle or control means
15 inspection and/or cleaning means (e.g., camera and/or rinsing nozzle)
15*a* rinsing head or rinsing nozzle
15*b* camera or camera system
15*c* power/data cable arranged within a cable channel
15*d* nozzles
15*e* cart body or cart housing
17 rinsing hose
17*a* first section of the rinsing hose 17b second section of the rinsing hose
18 hose coupling
19 fixing means for repeaters 50 (e.g. clips or clamps)
20 first transmission/receiver means (e.g., receiver means at the control means 10)
30 second transmission/receiver means (e.g., transmission means at the cleaning means 15)
31 hose port
40 stationary repeater or transmission/receiver means assigned to the control means 10
50 repeater
51 antenna or antenna system of the repeater 50
52 axial duct in the repeater 50
53 inner wall of the hose of the rinsing hose 17
54 liner at the hose inner wall 53
F wireless communication connection (e.g., WLAN connection)

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention. Furthermore, the foregoing describes the invention in terms of embodiments foreseen by the inventor for which an enabling description was available, notwithstanding that insubstantial modifications of the invention, not presently foreseen, may nonetheless represent equivalents thereto.

What is claimed is:

1. An inspection system for inspection or cleaning of pipes, the inspection system comprising:
   an inspection or cleaning means;
   a control means;
   a first transmission/receiver means assigned to the control means; and
   a second transmission/receiver means assigned to the inspection or cleaning means for wireless transmission of control or measurement data between the inspection or cleaning means and the control means;
   wherein a hose connects the inspection or cleaning means to the control means, wherein the hose comprises a rinsing hose having first and second rinsing hose sections, and wherein the inspection or cleaning means comprises a rinsing nozzle;
   wherein the rinsing nozzle comprises a camera coupled to the second transmission/receiver means operatively, and wherein images taken by the camera are transmittable to the first transmission/receiver means via the second transmission/receiver means wirelessly or wherein control commands intended for the camera or the rinsing nozzle are transmittable wirelessly via the first transmission/receiver means to the second transmission/receiver means; and
   further comprising at least one repeater having an axial duct, by means of which the first rinsing hose section is connectable to the second rinsing hose section, wherein for connecting the first rinsing hose section and the second rinsing hose section to the repeater, hose couplings are provided, and wherein a diameter of the axial duct is substantially as large as an inner diameter of the first rinsing hose section and the second rinsing hose section.

2. The inspection system according to claim 1, the at least one repeater further comprising an antenna system or at least one antenna, which is arranged operatively between the first transmission/receiver means and the second transmission/receiver means and being adapted to increase an operation range of a wireless communication connection established between the first transmission/receiver means and the second transmission/receiver means, wherein the wireless communication connection comprises a WLAN communication connection.

3. The inspection system according to claim 1, wherein the inspection or cleaning means can be coupled or connected to the control means via the hose, a rope, or a cable, and wherein the at least one repeater can be connected to the hose, at the rope, or at the cable.

4. The inspection system according to claim 3, wherein in addition to the hose, the rope, or the cable, an additional hose, an additional rope, or an additional cable is provided, which is insertable into the pipes, wherein at the additional hose, at the additional rope, or at the additional cable, the at least one repeater can be connected releasably.

5. The inspection system according to claim 3, wherein the first and second rinsing hose sections are separated from each other, wherein the at least one repeater (50) is arranged between the first and second rinsing hose sections and connects the first and second rinsing hose sections to each other.

6. The inspection system according to claim 1, wherein the repeater comprises a device for converting kinetic energy of rinsing water into electrical energy, wherein the device comprises at least one hydraulic turbine and at least one generator, wherein the at least one hydraulic turbine is arranged within the axial duct at least partially.

7. The inspection system according to claim 6, wherein the repeater comprises an accumulator, which is coupled to the at least one generator, and wherein the accumulator or the at least one generator supplies the repeater with electrical energy.

8. The inspection system according to claim 1, wherein the at least one repeater is integrated into a liner of the hose, or wherein the at least one repeater is arranged at a hose inner wall of the hose, and is surrounded by a watertight liner.

9. The inspection system according to claim 2, wherein an antenna of the at least one repeater is led to the outside at least partially through a liner of the hose, or wherein an antenna of the at least one repeater is formed by a material suitable for an antenna arranged at an outer wall of the hose.

10. The inspection system according to claim 1, wherein the at least one repeater further comprises fixing means, by means of which the at least one repeater is releasably connectable at the hose, in particular, the rinsing hose, at a cable, or at a rope.

11. The inspection system according to claim 1, wherein the at least one repeater is adapted to automatically increase or automatically decrease its transmission power.

12. A transmission/receiver means configured to:
   wirelessly transmit control or measurement data to an inspection or cleaning means assigned to the transmission/receiver means and a control means of the inspection system of claim 1; and establish a wireless communication connection to a further transmission/receiver means assigned to the control means.

13. The transmission/receiver means according to claim 12, wherein the transmission/receiver means is further configured to establish a wireless communication connection to a repeater arranged between the transmission/receiver means and the further transmission/receiver means.

14. An inspection or cleaning device, comprising
a transmission/receiver means according to claim 12;
an inspection or cleaning means which can be coupled to the transmission/receiver means; and
at least one selected from the group consisting of a cleaning nozzle, an inspection camera, an inspection vehicle or cart, and combinations thereof.

\* \* \* \* \*